US00PP18491P2

(12) United States Plant Patent
Hoogendoorn

(10) Patent No.: US PP18,491 P2
(45) Date of Patent: Feb. 19, 2008

(54) *ALSTROEMERIA* PLANT NAMED 'ZALSALEO'

(50) Latin Name: *Alstromeria hybrida*
Varietal Denomination: Zalsaleo

(75) Inventor: Cornelis Arie Hoogendoorn, Rijsenhout (NL)

(73) Assignee: Van Zanten Plants b.v., Hillegom (NL)

( * ) Notice: Subject to any disclaimer, the term of this patent is extended or adjusted under 35 U.S.C. 154(b) by 42 days.

(21) Appl. No.: 11/436,027

(22) Filed: May 17, 2006

(51) Int. Cl.
*A01H 5/00* (2006.01)

(52) U.S. Cl. ..... Plt./309

(58) Field of Classification Search ..... Plt./309
See application file for complete search history.

(56) References Cited

U.S. PATENT DOCUMENTS

PP11,331 P * 4/2000 Plevier ..... Plt./309
PP14,355 P2 * 12/2003 Hoogendoorn ..... Plt./309

* cited by examiner

*Primary Examiner*—Wendy C. Haas
(74) *Attorney, Agent, or Firm*—C. A. Whealy

(57) ABSTRACT

A new and distinct cultivar of *Alstroemeria* plant named 'Zalsaleo', characterized by its erect and strong flowering stems; vigorous growth habit; light pink and white-colored flowers; and excellent postproduction longevity.

1 Drawing Sheet

Botanical designation: *Alstroemeria hybrida.*
Cultivar denomination: 'Zalsaleo'.

BACKGROUND OF THE INVENTION

The present invention relates to a new and distinct cultivar of *Alstroemeria* plant, botanically known as *Alstroemeria hybrida,* commercially used as a cut flower *Alstroemeria,* and hereinafter referred to by the name 'Zalsaleo'.

The new *Alstroemeria* is a product of a planned breeding program conducted by the Inventor in Hillegom, The Netherlands. The objective of the breeding program is to create new cut flower *Alstroemeria* cultivars with desirable flower and plant qualities, attractive foliage and flower coloration and excellent postproduction longevity.

The new *Alstroemeria* originated from a cross-pollination made by the Inventor in Hillegom, The Netherlands in June, 1999, of a proprietary *Alstroemeria hybrida* selection identified as code number 97-388-2, not patented, as the female, or seed, parent with a proprietary *Alstroemeria hybrida* selection identified as code number 98-462-2, not patented, as the male, or pollen, parent. The cultivar Zalsaleo was discovered and selected by the Inventor as a flowering plant from within the progeny of the stated cross-pollination in a controlled environment in Hillegom, The Netherlands in April, 2000.

Asexual reproduction of the new *Alstroemeria* by root divisions in a controlled environment in Hillegom, The Netherlands since September, 2000, has shown that the unique features of this new *Alstroemeria* are stable and reproduced true to type in successive generations.

SUMMARY OF THE INVENTION

The cultivar Zalsaleo has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Zalsaleo'. These characteristics in combination distinguish 'Zalsaleo' as a new and distinct cultivar of *Alstroemeria:*

1. Erect and strong flowering stems.
2. Vigorous growth habit.
3. Light pink and white-colored flowers.
4. Excellent postproduction longevity.

Plants of the new *Alstroemeria* can be compared to plants of the parent selections. Plants of the new *Alstroemeria* differ from plants of the parent cultivars primarily in flower color and productivity.

Plants of the new *Alstroemeria* can be compared to plants of the *Alstroemeria hybrida* cultivar Virginia, disclosed in U.S. Plant Pat. No. 11,331. In side-by-side comparisons conducted in Hillegom, The Netherlands, plants of the new *Alstroemeria* differed from plants of the cultivar Virginia primarily in flower color as plants of the cultivar Virginia had white-colored flowers with numerous stripes.

BRIEF DESCRIPTION OF THE PHOTOGRAPH

The accompanying colored photograph illustrates the overall appearance of the new *Alstroemeria,* showing the colors as true as it is reasonably possible to obtain in colored reproductions of this type. Colors in the photograph may differ slightly from the color values cited in the detailed botanical description which accurately describe the colors of the new *Alstroemeria.* The photograph comprises a side perspective view of a typical flowering stem of 'Zalsaleo'.

DETAILED BOTANICAL DESCRIPTION

The aforementioned photograph and following observations and measurements describe plants of the new *Alstroemeria* grown in Rijsenhout, The Netherlands in a glass-covered greenhouse in ground beds. During the production of the plants, day temperatures ranged from 15° C. to 20° C., night temperatures ranged from 10° C. to 15° C. and light levels averaged 5,000 lux. Plants used for the photograph and description were about one year-old. The photograph and the description were taken during the spring. Color references are made to The Royal Horticultural Society Colour Chart, 1995 Edition, except where general terms of ordinary dictionary significance are used.

Botanical classification: *Alstroemeria hybrida* cultivar Zalsaleo.

Parentage:

*Female, or seed, parent.*—Proprietary *Alstroemeria hybrida* selection identified as code number 97-388-2, not patented.

*Male or pollen parent.*—Proprietary *Alstroemeria hybrida* selection identified as code number 98-462-2, not patented.

Propagation:

*Type.*—By root divisions.

*Root description.*—Fibrous, fleshy, thick; white, close to 155D, in color.

*Rooting habit.*—Freely branching.

*Rhizomes.*—Shape: Elongate; rounded. Length: About 10 cm to 30 cm. Diameter: About 3 cm to 10 mm. Texture: Smooth. Color: Close to 155D.

Plant description:

*Plant habit.*—Upright; freely branching, bushy appearance. Vigorous growth habit.

*Time from planting to harvest of cut flowers.*—About 80 to 90 days.

*Number of flowering stems produced per year.*—About 240 to 260.

*Plant height.*—About 90 cm to 130 cm.

*Plant diameter (spread).*—About 25 cm to 30 cm.

Flowering stem description:

*Aspect.*—Erect.

*Length.*—About 1.2 meters.

*Diameter.*—About 8 mm to 10 mm.

*Internode length.*—About 2 cm to 8 cm.

*Strength.*—Strong.

*Texture.*—Glabrous.

*Color.*—Close to 138A.

Foliage description:

*Appearance.*—Leaves asymmetrical; sessile.

*Length.*—About 15 cm to 19 cm.

*Width.*—About 2 cm to 5 cm.

*Shape.*—Lanceolate.

*Apex.*—Acute.

*Base.*—Attenuate.

*Margin.*—Entire; slightly undulate.

*Texture, upper and lower surfaces.*—Smooth, glabrous.

*Venation pattern.*—Parallel.

*Color.*—Developing and fully developed foliage, upper surface: Close to 137A; venation, similar to lamina. Developing and fully developed foliage, lower surface: Close to 137B; venation, similar to lamina.

Flower description:

*Flower type and habit.*—Single cup-shaped flowers arranged in compound umbels. Perianth segments separate. Freely and continuously flowering. Flowers not persistent.

*Natural flowering season.*—Flowering continuous during the spring in The Netherlands.

*Fragrance.*—None detected.

*Flower longevity on the plant.*—About four weeks.

*Flower longevity as a cut flower.*—About 20 to 25 days.

*Flower buds (showing color).*—Length: About 3 cm to 5 cm. Diameter: About 1 cm to 2 cm. Shape: Roughly ovoid. Color: Greenish.

*Umbel height.*—About 15 cm to 20 cm.

*Umbel diameter.*—About 20 cm to 25 cm.

*Number of flowers per umbel.*—About 15 to 20.

*Flower length (height).*—About 5 cm to 7 cm.

*Flower diameter.*—About 6 cm to 7 cm.

*Flower depth.*—About 6 cm to 8 cm.

*Perianth.*—Arrangement: Six arranged in two whorls, each whorl with two lateral and one median segments. Size, outer perianth: Length, lateral segments: About 6 cm to 7 cm. Width, lateral segments: About 3 cm to 4 cm. Length, median segment: About 6.5 cm to 7.5 cm. Width, median segment: About 3 cm to 3.5 cm. Size, inner perianth: Length, lateral segments: About 6.5 cm to 7.5 cm. Width, lateral segments: About 1.5 cm to 2 cm. Length, median segment: About 5.5 cm to 6.5 cm. Width, median segment: About 1.5 cm to 2 cm. Shape, outer perianth, lateral and median segments: Obovate. Shape, inner perianth, lateral and median segments: Oblanceolate. Apex, outer perianth, lateral and median segments: Emarginate. Apex, inner perianth, lateral and median segments: Acute. Base, outer and inner perianths, lateral and median segments: Attenuate. Margin, outer and inner perianths, lateral and median segments: Entire; weakly undulate. Texture, outer and inner perianths, lateral and median segments: Smooth, glabrous. Color, outer perianth: When opening and fully opened, lateral segments, upper surface: Close to 155D; splotch, close to 61C; apex, greenish. When opening and fully opened, lateral segments, lower surface: 61C; towards the apex, close to 155D; apex and venation, greenish. When opening and fully opened, median segment, upper surface: Close to 155D; splotch, close to 61C; apex, greenish. When opening and fully opened, median segment, lower surface: 61C; towards the apex, close to 155D; apex and venation, greenish. Color, inner perianth: When opening and fully opened, lateral segments, upper surface: Towards the apex, close to 155D; center, close to 3C; apex, greenish; few stripes, purplish close to 187A. When opening and fully opened, lateral segments, lower surface: Close to 155D; center, close to 3C; base, close to 61C; apex and venation, greenish. When opening and fully opened, median segment, upper surface: Close to 155D; splotch, 61C; apex, greenish. When opening and fully opened, median segment, lower surface: Close to 155D; splotch, 61C; midvein, greenish.

*Peduncles.*—Length: About 1 cm to 7 cm. Diameter: About 3 mm to 5 mm. Strength: Strong. Angle: About 15° C. to about 20° C. from vertical. Texture: Smooth, glabrous. Color: Close to 138A.

*Reproductive organs.*—Stamens: Quantity per flower: Six. Anther shape: Elliptical. Anther length: About 8 mm. Anther diameter: About 3 mm. Anther color: Close to 166A. Pollen amount: Abundant. Pollen color: Close to 83A. Pistils: Quantity per flower: One. Style length: About 4.5 cm to 5 cm. Style color: Towards the apex, light purple; towards the base, white. Stigma color: Pinkish purple. Ovary color: Close to 138A.

*Fruit.*—Shape: Globular. Color: Brownish.

Disease/pest resistance: Plants of the new *Alstroemeria* have not been observed to be resistant to pathogens and pests common to *Alstroemeria*.

Temperature tolerance: Plants of the new *Alstroemeria* have been observed to tolerate temperatures from about −5° C. to about 40° C.

It is claimed:

1. A new and distinct *Alstroemeria* plant named 'Zalsaleo' as illustrated and described.

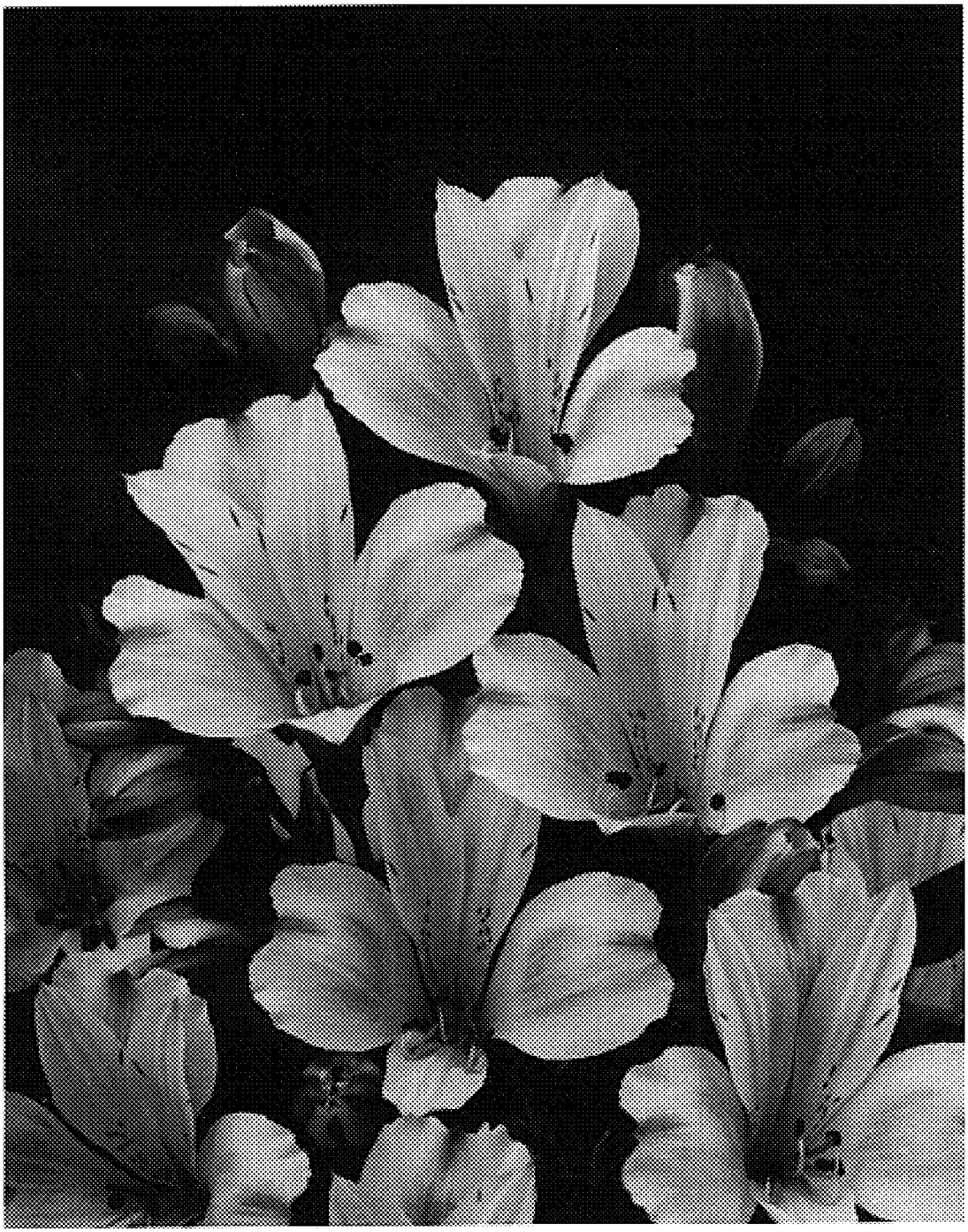

* * * * *